United States Patent [19]

Perboni et al.

[11] Patent Number: 5,426,104

[45] Date of Patent: Jun. 20, 1995

[54] TRICYCLIC CARBAPENEM COMPOUNDS, METHODS OF PREPARATION AND METHODS OF USE

[75] Inventors: Alcide Perboni; Daniele Donati; Giorgio Tarzia, all of Verona, Italy

[73] Assignee: Glaxo SpA, Verona, Italy

[21] Appl. No.: 107,848

[22] PCT Filed: Mar. 2, 1992

[86] PCT No.: PCT/EP92/00458

§ 371 Date: Sep. 21, 1993

§ 102(e) Date: Sep. 21, 1993

[87] PCT Pub. No.: WO92/15288

PCT Pub. Date: Sep. 17, 1992

[30] Foreign Application Priority Data

Mar. 7, 1991 [GB] United Kingdom ............... 9104838

[51] Int. Cl.$^6$ .................. A01N 43/00; A61K 31/395
[52] U.S. Cl. ................................. 514/210; 540/302
[58] Field of Search ..................... 514/210; 540/302

[56] References Cited

U.S. PATENT DOCUMENTS 4,374,848  2/1983  Christensen .
5,068,232  11/1991 Ziegler, Jr. et al. .

FOREIGN PATENT DOCUMENTS 0416952  3/1991  European Pat. Off. .
0416953  3/1991  European Pat. Off. .
0422596  4/1991  European Pat. Off. .
2311328  3/1973  Germany .

OTHER PUBLICATIONS

CA 62:7675e.
Green et al, Protective Groups in Organic Synthesis, 2nd edition, pp. 224–231.

*Primary Examiner*—Johann Richter
*Assistant Examiner*—Rebecca Cook
*Attorney, Agent, or Firm*—Bacon & Thomas

[57] ABSTRACT

Compounds of general formula (I)

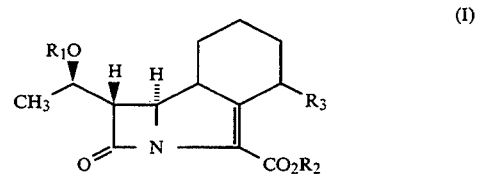

in which
R$_1$ represents a hydrogen atom or a hydroxyl protecting group, R$_2$ represents a hydrogen atom or a carboxyl protecting group, and R$_3$ represents the group N(R$_4$)—CH=NR$_5$ wherein R$_4$ represents a hydrogen atom and R$_5$ represents a hydrogen atom; and salts, metabolically labile esters and solvates thereof and a process for their production. The compounds of formula (I) are either antibacterial agents and or useful intermediates for the preparation of antibacterial agents.

20 Claims, No Drawings

TRICYCLIC CARBAPENEM COMPOUNDS, METHODS OF PREPARATION AND METHODS OF USE

This application is a 371 of PCT/EP92/00458, filed Mar. 2, 1992.

This invention relates to heterocyclic derivatives having antibacterial activity, to processes for their preparation, to compositions containing them, and to their use in medicine.

Thus the present invention provides compounds of the general formula (I)

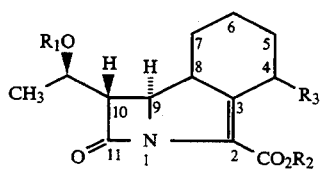

in which $R_1$ represents a hydrogen atom or a hydroxyl protecting group;

$R_2$ represents a hydrogen atom, a carboxyl protecting group or a cation derived from an inorganic base or an organic base;

$R_3$ represents the group $-N(R_4)-CH=NR_5$ in which $R_4$ represents a hydrogen atom and $R_5$ represents a $C_{1-4}$alkyl group or $R_4$ represents a $C_{1-4}$alkyl group and $R_5$ represents a hydrogen atom;

and salts, metabolically labile esters and solvates thereof.

Salts of compounds of formula (I) include acid addition salts of such compounds and internal salts formed with the carboxylic acid grouping ($R_2$=H).

In addition to the fixed stereochemical arrangement as defined in formula (I) the molecule contains a further asymmetric carbon atom at the 8-position, and another at the 4-position. It will be appreciated that all stereoisomers including mixtures thereof arising from these additional asymmetric centres, are within the scope of the compounds of formula (I).

The compounds of formula (I) are antibacterial agents and/or of use as intermediates for the preparation of other active compounds within the general formula (I). Compounds wherein $R_1$ represents a hydroxyl protecting group and/or wherein $R_2$ represents a carboxyl protecting group are in general intermediates for the preparation of other compounds of formula (I).

Suitable hydroxyl protecting groups $R_1$ and carboxyl protecting groups $R_2$ include those which may be removed by hydrolysis under buffered conditions or under non-aqueous conditions.

When the group $OR_1$ is a protected hydroxyl group this is conveniently an ether or an acyloxy group. Examples of particularly suitable ethers include those in which $R_1$ is a hydrocarbylsilyl group such as trialkylsilyl, e.g. trimethylsilyl or t-butyldimethylsilyl. When the group $OR_1$ represents an acyloxy group then examples of suitable groups $R_1$ includes alkanoyl e.g. acetyl, pivaloyl; alkenoyl e.g. allylcarbonyl; aroyl e.g. p-nitrobenzoyl; alkoxycarbonyl e.g. t-butoxycarbonyl; haloalkoxycarbonyl e.g. 2,2,2-trichloroethoxycarbonyl, or 1,1,1-trichloro-2-methyl-2-propoxycarbonyl; aralkyloxycarbonyl e.g. benzyloxycarbonyl or P-nitrobenzyloxycarbonyl; or alkenyloxycarbonyl e.g. allyloxycarbonyl.

A particularly convenient protecting group $R_1$ is t-butyldimethylsilyl.

Examples of suitable carboxyl protecting groups include arylmethyl groups such as benzyl, p-nitrobenzyl or trityl, or alkenyl groups such as allyl or substituted allyl, t-butyl, haloalkyl e.g. trichloroethyl or trialkylsilylalkyl e.g. trimethylsilylethyl. Preferred protecting groups $R_2$ include arylmethyl e.g. benzyl or allyl.

Particularly useful compounds of formula (I) for use in medicine as antibacterial agents are those in which the group $R_1$ represents a hydrogen atom and $R_2$ represents a hydrogen atom or a physiologically acceptable cation, or an internal salt thereof; or acid addition salts of compounds wherein $R_2$ represents a hydrogen atom. These compounds exhibit antibacterial activity against a wide range of gram positive and gram negative, aerobic and anaerobic pathogenic microorganisms.

Where $R_2$ is a physiologically acceptable cation, suitable cations include those of alkali metals (e.g. sodium or potassium), alkaline earth metals (e.g. calcium), amino acids (e.g. lysine and arginine) and organic bases (e.g. procaine, phenylbenzylamine, dibenzylethylenediamine, ethanolamine, diethanolamine, and N-methyl glucosamine).

Where $R_2$ is a cation that is not physiologically acceptable then such compounds may be useful as intermediates for the preparation and/or isolation of other compounds of the invention.

Suitable acid addition salts of compounds of formula (I) include those formed with inorganic acids such as hydrochloric acid, hydrobromic acid, sulphuric acid, and phosphoric acid, organic acids such as acetic acid, maleic acid, fumaric acid, formic acid, succinic acid, citric acid, benzoic acid and tartaric acid and organic sulphonic acids such as p-toluenesulphonic acid and methanesulphonic acid.

The general formula (I) as drawn includes at least 4 stereoisomers and mixtures thereof and these may be represented by the formulae (1a, 1b, 1c and 1d).

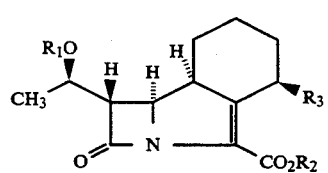

1a

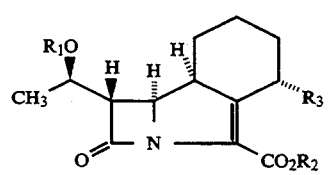

1b

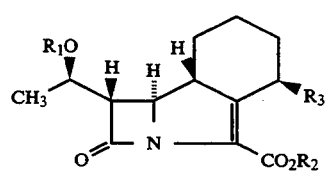

1c

-continued

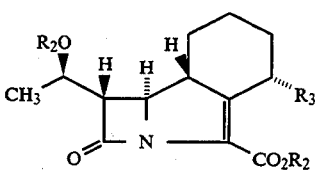

1d

The wedge shaped bond ◂ indicates that the bond is above the plane of the paper. The broken bond ┄ indicates that the bond is below the plane of the paper.

The configuration shown for the carbon atom at the 8-position in formulae 1a and 1b is hereinafter referred to as the β configuration and in formulae 1c and 1d as the α configuration.

The configuration shown for the carbon at the 4 position in formulae 1b and 1d is hereinafter referred to as the α configuration and in formulae 1a and 1c as the β configuration.

In general, in the specific compounds named below, the β-configuration at the 8-position corresponds to the S isomer and the β-configuration at the 4-position to the R isomer. The α configuration at the 8-position corresponds to the R isomer and the α-configuration at the 4-position corresponds to the S isomer. The assignment of the R or S configuration at the 4- and 8-positions have been made according to the rules of Cahn. Ingold and Prelog, Experientia 1956, 12, 81.

When $R_4$ represents a $C_{1-4}$alkyl group and examples of such groups include methyl, ethyl, propyl and butyl.

When $R_5$ represents a $C_{1-4}$alkyl group examples of such groups include methyl, ethyl, propyl and butyl.

A preferred group of compounds of formula I are those in which the carbon atom at the 8-position is in the β configuration as shown in formulae 1a and 1b above. Within this group those compounds in which the carbon atom at the 4-position is in the α configuration as shown in formula 1b above are particularly preferred.

A further preferred group of compounds of the invention are those in which the group $R_4$ represents a methyl group and $R^5$ represents a hydrogen atom or $R^4$ represents a hydrogen atom and $R^5$ represents a methyl group. More particularly preferred are those compounds wherein $R^4$ represents a methyl group.

A particularly preferred group of compounds of formula (I) are those in which the carbon atom at the 8-position is in the β configuration and the carbon atom at the 4-position in the α configuration, $R_1$ represents a hydrogen atom, and $R_2$ represents a hydrogen atom or a physiologically acceptable cation and metabolically labile esters, salts and solvates thereof.

Specific preferred compounds include (4S,8S,9R,10S,12R)-4-(N-methylformamidino)-10-(1-hydroxyethyl)-11-oxo-1-azatricyclo [7.2.0.0$^{3,8}$] undec-2-ene-2-carboxylic acid and salts thereof e.g. sodium or potassium salts or the internal salt thereof, or an acid addition salt thereof.

Compounds according to the invention not only exhibit a broad spectrum of antibacterial activity against a wide range of pathogenic microorganisms but also have a very high resistance to all β-lactamases. Compounds of the invention are also relatively stable to renal dehydropeptidase.

Compounds of the invention have been found to exhibit useful levels of activity against strains of *Staphylococcus epidermidis, Staphylococcus aureus, Streptococcus faecalis, Streptococcus pneumoniae, Streptococcus pyogenes, Streptococcus agalactiae, Escherichia coli, Pseudomonas aeruginosa, Klebisiella pneumoniae, Klebsiella oxytoca, Citrobacter diversus, Citrobacter freundii, Enterobacter cloacae, Enterobacter aerogenes, Proteus mirabilis, Proteus rettgeri, Proteus vulgaris, Morganella morganii, Serratia marcescens, Acinetobacter calcoaceticus, Branhamella catarrhalis, Haemophilus influenzae, Haemophilus parainfluenzae, Clostridium perfringens* and *Bacteriodes fragilis*.

The compounds of the invention may therefore be used for treating a variety of diseases caused by pathogenic bacteria in human beings and animals.

Thus, according to another aspect of the present invention, we provide a compound of formula (I) for use in the therapy or prophylaxis of systemic or topical bacterial infections in a human or animal subject.

According to a further aspect of the invention we provide the use of a compound of formula (I) for the manufacture of a therapeutic agent for the treatment of systemic or topical bacterial infections in a human or animal body.

According to a yet further aspect of the invention we provide a method of treatment of the human or non-human animal body to combat bacterial infections which method comprises administering to the body an effective amount of a compound of formula (I).

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in conventional manner with the aid of one or more suitable carriers or excipients. The compositions of the invention include those in a form especially formulated for parenteral, oral, buccal, rectal, topical, implant, ophthalmic, nasal or genitourinary use.

The compounds according to the invention may be formulated for use in human or veterinary medicine by injection (e.g. by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

The compounds according to the invention may be formulated for topical administration, for use in human and veterinary medicine, in the form of ointments, creams, gels, lotions, shampoos, powders, (including spray powders), pessaries, tampons, sprays, dips, aerosols, drops (e.g. eye ear or nose drops) or pour-ons.

Aerosol sprays are conveniently delivered from pressurised packs, with the use of a suitable propellant, eg dichlorodifluoromethane, trichlorofluoromethane, dichlorotetrafluoroethane, carbon dioxide or other suitable gas.

For topical administration by inhalation the compounds according to the invention may be delivered for use in human or veterinary medicine via a nebuliser.

The pharmaceutical compositions for topical administration may also contain other active ingredients such as corticosteroids or antifungals as appropriate.

The compositions may contain from 0.01-99% of the active material. For topical administration, for example, the composition will generally contain from 0.01-10%, more preferably 0.01-1% of the active material.

For systemic administration the daily dose as employed for adult human treatment will range from 5-100 mg/kg body weight, preferably 10-60 mg/kg body weight, which may be administered in 1 to 4 daily doses, for example, depending on the route of administration and the condition of the patient. When the composition comprises dosage units, each unit will preferably contain 200 mg to 1 g of active ingredient.

The duration of treatment will be dictated by the rate of response rather than by arbitrary numbers of days.

The compounds of formula (I) may be prepared by reaction of a compound of formula (II) wherein $R_1$, $R_2$ and $R_4$ are as defined in formula (I).

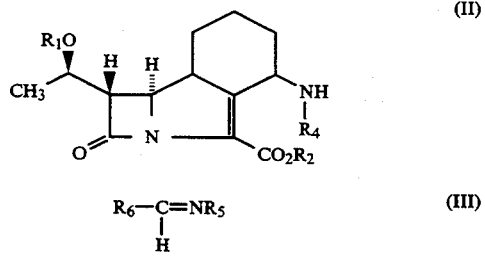

with an amidinating agent serving to introduce the group $R_3$ as defined in above in formula (I). Suitable amidinating agent include compounds of formula (III) wherein $R_5$ has the meanings as defined above in formula (I) and $R_6$ represents a leaving group such as a halogen atom, for example a chlorine or bromine atom or a $C_{1-4}$ alkoxy group such as methoxy or ethoxy, or an optionally substituted benzyloxy group such as benzyloxy or p-nitro benzyloxy, followed as necessary or desired by removal of any protecting group $R_1$ and/or $R_2$. The reaction is conveniently carried out in a solvent such as tetrahydrofuran, dioxane, dimethyl formamide, dimethylsulphoxide, water or mixtures thereof and at a temperature within the range 0°-30° C. It is convenient to carry out the reaction using a compound of formula (III) in which $R_6$ is an alkoxy or optionally substituted benzyloxy group in the form of an acid addition salt thereof such as the hydrochloride salt and in this situation a suitable base such as sodium hydroxide solution is added to the reaction mixture.

Where the groups $R_1$ and/or $R_2$ are hydroxyl and carboxyl protecting groups these may be removed by conventional procedures and in any order. More preferably however the hydroxyl protecting group $R_1$ is removed prior to the removal of the carboxyl protecting group. Such removal of the protecting groups is a further feature of the invention.

The hydroxyl protecting groups may be removed by well known standard procedures such as those described in Protective Groups in Organic Chemistry, pages 46–119, Edited by J F W McOmie (Plenum Press, 1973). For example when $R_1$ is a t-butyldimethylsilyl group, this may be removed by treatment with tetrabutylammonium fluoride and acetic acid. This process is conveniently carried out in a solvent such as tetrahydrofuran. Similarly when $R_1$ is a trichloroethoxycarbonyl group this may be removed by treatment with zinc and acetic acid.

The carboxyl protecting group $R_2$ may also be removed by standard processes such as those described in Protective Groups in Organic Chemistry, pages 192–210, Edited by J F W McOmie (Plenum Press 1973). For example when $R_2$ represents an arylmethyl group this may be removed by conventional procedures using hydrogen and a metal catalyst e.g. palladium. When the group $R_2$ represents an allyl or substituted allyl group then this is preferably removed by treatment with an allyl acceptor in the presence of tetrakis(triphenylphosphine) palladium and optionally in the presence of triphenylphosphine. Suitable allyl acceptors include sterically hindered amines such as tertbutylamine, cyclic secondary amines such as morpholine or thiomorpholine, tertiary amines such as triethylamine, aliphatic or cycloaliphatic β-dicarbonyl compounds such as acetylacetone, ethyl acetoacetate or dimedone, or alkanoic acids or alkali metal salts thereof such as acetic acid, propionic acid or 2-ethyl hexanoic acid or the potassium or sodium salt thereof.

A particularly useful allyl acceptor is dimedone.

The reaction is preferably carried out in an inert solvent such as an ether e.g. diethyl ether or tetrahydrofuran, an alkanol e.g. ethanol, an ester e.g. ethyl acetate or a halohydrocarbon e.g. methylene chloride, or mixtures thereof. The reaction is conveniently carried out in the temperature range 0°–40° more particularly at room temperature.

Compounds of the invention in which the group $R_2$ is a physiologically acceptable cation may be prepared from compounds of the invention in which $R_2$ is hydrogen by treatment with a suitable base. Conveniently the salt is formed in solution and then if required precipitated by the addition of a non-solvent e.g. a non polar aprotic solvent. Alternatively the sodium or potassium salt may be prepared by treating a solution of a compound of formula (I) in which $R_2$ represents a hydrogen atom with a solution of sodium or potassium 2-ethylhexanoate in a non-polar solvent such as diethyl ether.

Compounds of formula (II) may be prepared using the processes described in EP-A-0416953A2.

Compounds of formula (II) in which the groups $R_1$ and $R_2$ and $R_4$ have the meanings defined above may be prepared by cyclisation of a compound of formula (IV)

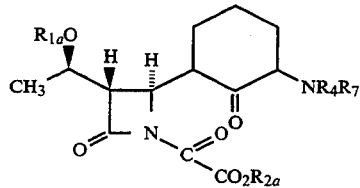

(IV)

in which the group $R_7$ is an allyloxycarbonyl group and the groups $R_{1a}$ and $R_{2a}$ are hydroxy and carboxyl protecting groups as defined above for $R_1$ and $R_2$, followed by removal of the allyloxycarbonyl grouping and if desired or necessary removal of the hydroxy and or carboxyl protecting groups.

The cyclisation of a compound of formula (IV) is conveniently carried out by heating in the presence of an organic phosphite. The reaction is preferably carried out in a solvent or mixture of solvents at a temperature within the range 60°–200°. Suitable solvents include hydrocarbons with an appropriate boiling point, for example aromatic hydrocarbons, such as toluene or xylene.

Suitable organic phosphites include acyclic and cyclic trialkylphosphites, triarylphosphites and mixed alkylarylphosphites. Particularly useful organic phosphites are the trialkylphosphites e.g. triethylphosphite or trimethylphosphite.

The allyloxycarbonyl group $R_7$ may be removed by conventional means, for example using the conditions described above for converting an allyl ester into the corresponding carboxylic acid.

If required the hydroxyl and carboxyl protecting groups $R_1$ and or $R_{2a}$ may be removed using the procedures described above.

Compounds of formula (IV) may be prepared by treating a compound of formula (V) in which the group $R_{1a}$, $R_4$ and $R_7$ have the meanings given above with an activated derivative of the acid (VI) in which $R_{2a}$ is a protected carboxyl group as defined above.

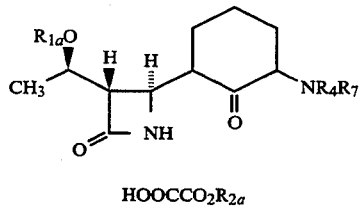

(V)

HOOCCO$_2$R$_{2a}$ (VI)

Suitable activated derivatives of the acid (VI) includes the corresponding acid halides e.g. acid chloride.

When the acid halide is used as the activated derivative of the acid (VI) then the reaction is preferably carried out in the presence of an acid acceptor such as a tertiary organic base for example pyridine or a trialkylamine in an aprotic solvent such as dichloromethane.

Compounds of formula (V) in which $R_{1a}$ $R_4$ and $R_7$ have the meanings defined above may be prepared by the processes described in EP-A-0416953A2.

Compounds of formula (V) may also be prepared from the epoxide (VII)

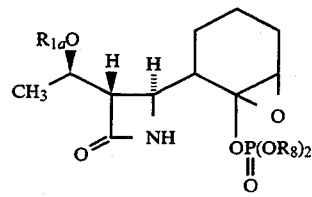

(VII)

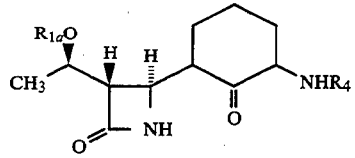

(VIII)

wherein $R_{1a}$ is a hydroxyl protecting group and $R_8$ is a $C_{1-4}$alkyl group by reaction with the amine $R_4NH_2$ in a suitable solvent such as ethyl acetate followed by reaction of the resultant keto amino (VIII) with allylchloroformate in the presence of a tertiary base such as triethylamine.

The epoxide (VII) may be prepared by oxidation of the cyclohexene derivative (IX)

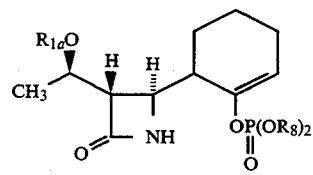

(IX)

The oxidation may be carried out using a suitable per acid such as metachloroperbenzoic acid in a solvent such as dichloromethane.

The cyclohexene (IX) may be prepared by treating the ketone (X) in which $R_{1a}$ is a hydroxyl protecting groups and $R_9$ is a $C_{1-4}$alkyl group

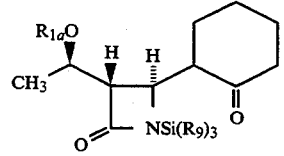

(X)

with a strong base such as a potassium or lithium bis(-trimethylsilylamide) and then reacting the enolate ion thus formed with the chlorophosphate $Cl(O)P(OR_8)_2$ followed by hydrolysis of the N-trialkyl silyl protecting group $((Si(R_9)_3))$.

The compounds of formula (X) may be prepared by the methods described in EP-A-0416953A.

The compounds of formula (III) are either known compounds or may be prepared by analogus routes. For example compounds of formula (III) in which $R_6$ represents a halogen atom may be prepared by treating the corresponding amide HCONHR$_5$ with the appropriate phosphorus pentahalide e.g. PCl$_5$ or PBr$_5$.

The compounds of formula (III) in which $R_6$ represents an alkoxy or optionally substituted benzyloxy group may be prepared by conventional routes known for preparing such imidoesters. For example the compound of formula (III) in which $R_6$ represents a halogen atom may be converted into a compound of formula (III) in which $R_6$ is a $C_{1-4}$alkoxy or optionally substituted benzoyloxy group by reaction with the corresponding alkoxide $R_6O^-$. Alternatively such compounds may be prepared from the amide $HCONHR_5$, for example by reaction with the alcohol $R_6OH$ in the presence of a suitable acid chloride, or by reaction of the amide with the fluoroborate $(R_6)_3O^+BF_4$.

In any of the formulae (I) to (X) shown above when there is an asymmetric carbon atom and no specific configuration is shown then the formula includes all possible configurations.

Specific stereoisomers of the compounds of formula (I) as defined in formulae 1a, 1b, 1c and 1d, essentially free of the other stereoisomers may be prepared by using the general processes described above starting with the appropriate stereoisomer of formula (V).

The processes described above for preparing the compounds of formula (V) will in general give a mixture of stereoisomers.

The individual stereoisomers of the compounds of formula (V) may be separated from each other by conventional techniques such as fractional crystallisation or more particularly by column chromatography, using for example a silica column, as illustrated in the relevant examples.

Alternatively the synthesis may be carried out starting with a mixture of 2 or more stereoisomers of formula (V) and the required specific stereoisomer separated at by conventional techniques at another stage in the synthesis. Thus the compounds may be separated by fractional crystallisation and or column chromatography.

In order that the invention may be more fully understood the following examples are given by way of illustration only.

In the Preparations and Examples, unless otherwise stated:

Melting points (m.p.) were determined on a Gallenkamp m.p. apparatus and are uncorrected. All temperatures refer to °C.

Infrared spectra were measured in chloroform-$d_1$ solutions on a FT-IR instrument. Proton Magnetic Resonance (1H-NMR) spectra were recorded at 300 MHz. Chemical shifts are reported in ppm downfield ($\delta$) from Me$_4$Si, used as an internal standard, and are assigned as singlets (s), doublets (d), doublet of doublets (dd) or multiplets (m).

HPLC refers to high performance liquid chromatography.

Phosphate buffer refers to an aqueous solution of monopotassium phosphate and dipotassium phosphate at a pH of 7 and a total phosphate concentration of 0.05M.

Intermediate 1

(3S, 4R)-1-(t-butyldimethylsilyl)-4-acetoxy-3[(R)-(t-butyldimethylsilyloxy)ethyl]azetidin-2-one To a stirred ice-cold solution of the (3S, 4R)-4-acetoxy-3[(R)-(1-t-butyldimethylsilyloxy)ethyl]-2-azetidinone (112 g) in dichloromethane (800 ml), t-butyldimethylchlorosilane (73 g) and triethylamine (80 ml) were added. The mixture was stirred at room temperature for 20 hr then washed with water (1 l) and brine (300 ml). The organic layer was dried and evaporated to give an oil (160 g) which was dissolved in a mixture of cyclohexane/ethyl acetate (95/5) (1600 ml) and treated with silica gel (480 g). The suspension was stirred for 15 min then filtered. The solid was washed with cyclohexane/ethyl acetate (95/5:4.81) and the solvent evaporated to give the title compound (110 g) as a pale yellow oil. (Rf=0.85 petrol/diethyl ether=2/1) IR(CDCl$_3$)V$_{max}$ (cm$^{-1}$): 1747(C=O) H$^1$-NMR (CDCl$_3$):6.14(d), 4.15(m), 3.07(dd), 2.03(s), 1.2(d), 0.9(s), 0.84(s), 0.22(s), 0.055(s), 0.35(s), 0.005(s)ppm.

Intermediate 2

(3S, 4R)-1-(t-butyldimethylsilyl-3-[(R)-1-(t-butyldimethylsilyloxy)ethyl]-4-[2'-(1'-oxo-cyclohexyl)]azetidin-2-one Stannic chloride (35.4 ml) was added dropwise to stirred acetonitrile (400 ml) under nitrogen atmosphere at −40° C., a white solid formed together with white fumes which were eliminated by nitrogen flushing. The obtained suspension was allowed to rise to −10° C. then a solution of 1-trimethylsilyloxycyclohexene (60.6 ml) and compound of Intermediate (1) (110 g) in acetonitrile (300 ml) was added in 10 minutes. The yellow solution was stirred at 0° C. for 10 min then poured into a stirred, ice-cold, mixture of a 10% aq solution of sodium hydroxide (1 l), diethyl ether (1 l) and ice (500 g). The organic layer was separated, washed again with sodium hydroxide (500 ml), then with a saturated solution of ammonium chloride, dried and evaporated to give a yellow solid (117.7 g). The solid was dissolved at 40° C. in isopropanol (300 ml) cooled to room temperature, water (300 ml) was added slowly under stirring to obtain a solid which was stirred at 0° C. for 30 min. The solid was filtered, washed with a 1 to 1 mixture of isopropanol/water (100 ml) and dried under vacuum at 40° C. for 15 hr to afford the title compound (76 g) as a mixture of 2'R and 2'S isomers in a ratio of 70% to 30% (the ratio between the two isomers was determined by HPLC using hexane/ethanol (99/1) as eluant).

Intermediate 3

(3S, 4R, 6'R)-1-t-butyldimethylsilyl-3-[(R)-1-(t-butyldimethylsilyloxy)ethyl]-4-[6'-(1'-diethoxyphosphinyloxycyclohex-1'-ene]azetidin-2-one A 1M solution of lithium bis(trimethylsilyl)amide in hexane (9 ml) was added to tetrahydrofuran (15 ml), the mixture was cooled to −70 C. under nitrogen, then the intermediate 2 (1.9 g) dissolved in tetrahydrofuran (10 ml) was added over 10 min. The obtained solution was stirred for 45 min, then diethyl chlorophosphonate (1.4 ml) was added over 2 min. The reaction mixture was stirred for 30 min, allowed to warm to −20 C. then poured into a saturated ammonium chloride solution and the resulting mixture extracted with diethyl ether. The organic layer was washed with a 5% ice-cold solution of acetic acid, aqueous solution of sodium hydrogen carbonate and brine, dried and evaporated to give a yellow oil which was purified on silica gel (rf=0.65 diethyl ether) to afford the title compound (1.8 g) as a colourless oil IR 1732(C=O), 1670(C=C) NMR: 5.73(m), 4.2–4(m), 3.83(m), 3.02(dd), 2.68(m), 2.09(m), 1.79–1.45(m), 1.34(t), 1.25(d), 0.96(s), 0.88(s), 0.30(s), 0.20(s), 0.087(s) and 0.066(s).

Intermediate 4

(3S,4R,6'R)-3-[(R)-1-(t-butyldimethylsilyloxyl)ethyl-4-[6'-(1'-diethoxyphosphinyloxycyclohex-1'-ene]azetidin-2-one Intermediate 3 (1 g) was dissolved at room temperature in methanol (25 ml) and treated with potassium fluoride (500 mg). The reaction mixture was stirred for 30 min. Then the solvent was partially evaporated under reduced pressure. The obtained thick suspension was poured into a saturated ammonium chloride solution and the resulting mixture extracted with diethyl ether. The organic layer was washed with brine, dried and evaporated to give the title compound (750 ml) as a pale yellow oil (rf=0.6 ethyl acetate). IR: 1755(C=O), 1676(C=C) NMR: 5.99(m), 5.69(m), 4.25–4.10(m), 4.06(dd), 3.04(dd), 2.57(m), 1.9–1.5(m), 1.33(t), 1.21(d), 0.87(s) and 0.076(s).

Intermediate 5

(3S,4R,6'R,2'R,1'S)-3-[(R)-1-(t-butyldimethylsilyloxy)ethyl-4-[6'-(1'-diethoxyphosphinyloxycyclohex-2'-ene oxide]azetidin-2-one Intermediate 4 (700 mg) was dissolved in dichloromethane (25 ml) at 0 C. Sodium hydrogen carbonate (250 mg), and metachloroperbenzoic acid (700 mg) were added. The obtained suspension was stirred at 0 C. for 1 hr, at room temperature for 1 hr then poured into an ice cold 3% aqueous sodium sulphite solution. The organic layer was separated and evaporated at 20 C. to give an oil which was dissolved in ethyl acetate and washed with a dilute ice-cold solution of sodium hydroxide, water and brine, dried and evaporated to give a yellow oil. The crude compound was purified on silica gel (rf=0.5 ethyl acetate) to afford the pure title compound (400 mg). IR: 3416(NH), 1757(C—O) NMR: 5.91(m), 4.25(m), 4.21(dd), 4.12(m), 3.79(m), 3.08(t), 2.49(m), 2.0–1.9(m), 1.8–1.7(m), 1.65–1.45(m), 1.45–1.3(m) 1.34(mn), 1.24(d), 0.88(s), 0.087(s) and 0.081(s).

Intermediate 6

(3S,4R)-3-((R)-1-(t-butyldimethylsilyloxy)ethyl)-4-((1'S,2'S,6'R)-2'-N-allyloxycarbonyl-N-methylamino)-1'-oxocyclohex-6'-yl)azetldin-2-one To a solution of Intermediate 5 (49 g) of ethylacetate (500 ml) with potassium carbonate (213 g) at 0° under nitrogen was added methylamine (16 g, 40% water). The reaction mixture was stirred for 1 hour at 0° then the ethyl acetate was decanted and the residual solid was washed with ethyl acetate (100 ml). The organic solution was washed with water (3×600 ml) and brine (1×500 ml) dried, concentrated in vacuo to 500 ml and cooled to 0°. To the solution allyl chloroformate (17 ml) and triethylamine (22 ml) were added. The reaction mixture was stirred for 30 min at 0° then washed with a saturated aqueous solution of ammonium chloride (300 ml), water (2×500 ml), brine (300 ml) dried and evaporated in vacuo. The residue was purified by trituration at reflux in petroleum ether (250 ml) to obtain the title compound as a white powder (24.9 g; m.p. 159°–161° t.l.c. diethyl ether/ethylacetate 3/2 Rf=0.68). IR$_{max}$ (CDCl$_3$) 3414, 1753, 1688 cm−1; H$^1$NMR (300 Mhz, CDCl$_3$) 6.2(bs), 5.9(m), 5.2(m), 4.6(m), 4.2(m), 4.0.4(m), 3.87(dd), 3.8(m), 3.17(dd), 2.86(s), 2.26(m), 1.8–1.2(m), 1.30(d), 0.89(s), 0.10(s), 0.09(s).

Intermediate 7

(4S,8S,9R,10S,12R)-4-(N-methylformamidino)-10-(1-hydroxyethyl)-11-oxo-1-azatricyclo[7.2.0.0$^{3,8}$]undec-2-ene-2-carboxylic acid The title compound was prepared from intermediate 6 as described in EP-A-0416953A2.

EXAMPLE 1

(4S,8S,9R,10S,12R)-4-(N-methylformamidino)-10-(1-hydroxyethyl)-11-oxo-1-azatricyclo[7.2.0.0$^{3,8}$]undec-2-ene-2-carboxylic acid (4S,8S,9R,10S,12R)-4-methylamino-10-(1-hydroxyethyl)-11-oxo-1-azatricyclo[7.2.0.0$^{3,8}$]undec-2-ene-2-carboxylic acid (83 mg) was dissolved in tetrahydrofuran (15 ml) and 75 ml of 0.05M, pH=7 phosphate buffer. The solution was stirred at 50 C. and the pH maintained at 8.5 by adding 1N sodium hydroxide solution whilst benzylformamidate hydrochloride (600 mg) was added over 45 min. The tetrahydrofuran was evaporated in vacuo, the aqueous solution was freeze dried and the residue purified by HPKC (Lichrosorb C18, 10μ, CH$_3$CN/H$_2$O=1/9) to give the title compound (43 mg). IR:V$_{max}$ (Nujol) 1761 cm−1; $^1$H-NMR δ(D$_2$O-Acetone): 7.76(s), 7.62(s), 5.18(m), 5.30(m), 4.2–4.0(m), 3.34(dd), 3.0–2.8(m+s), 2.2(m), 1.9–1.2(m) and 1.11(d) ppm.

EXAMPLE 2

(4S,8S,9R,10S,12R)-4-[(3'-methyl)formamidino)-10-(1-hydroxyethyl)-11-oxo-1-azatricyclo[7.2.0.0$^{3,8}$]undec-2-ene-2-carboxylic acid (4S,8S,9R,10S,12R)-4-amino-10-(1-hydroxyethyl)-11-oxo-1-azatricyclo[7.2.0.03.8]undec-2-ene-2-carboxylic acid (31 mg) was dissolved at 10° in a mixture of 0.05M phosphate buffer solution (34.4 ml) and tetrahydrofuran (15.6 ml) and the pH adjusted to 8.5 with 1N sodium hydroxide solution. p-Nitrobenzyl N-methyl formimidate hydrochloride (260 mg) was added in portions over 5 mins to the stirred solution and the pH of the reaction mixture was maintained at pH 8.5 by the addition of 1N sodium hydroxide solution. The reaction mixture was stirred for 30 min at 10° and the pH of the solution was adjusted to pH 7.5 by the addition of 1N hydrochloric acid. The solution was washed with diethyl ether (2×100 ml) and freeze dried. The crude solid was purified by HPLC (lichrosorb C18, S10) using acetonitrile/water 7/93 as eluant to obtain the title compound (14 mg, rt=1.5 min)

IR (nujul V$_{max}$ cm−1: 1589 (C=C. C=N), 1701 (C=O, 1763 (C=O B-lactam); 1H-NMR (300 MHz, D$_2$O): 7.59 (s), 5.28(m), 4.08(m), 3.97(dd), 3.28(dd), 2.93(s), 2.95–2.8(m), 1.88(m), 1.84–1.5(m), 1.38–1.2(m), 1.11(d).

Pharmacy Example

Dry Powder for Injection

Active ingredient (Compound of Example 1) 538 mg per vial.

Fill sterile vials with the sterile active ingredient. Purge the vial head space with sterile nitrogen; close the vials using rubber plugs and metal overseals (applied by crimping). The product may be constituted by dissolving in Water for Injection (10 ml) or other suitable sterile vehicle for injection shortly before administration.

The antibacterial activity of the compounds of the invention may be readily determined using conventional test procedures. For example the antibacterial activity of the compounds of the invention was determined using a standard microtiter broth serial dilution test. In this test the broth was incubated with approximately $10^5$ colony forming units of the test organism and incubated at 35° for 18 hours in the presence of test compound. Results obtained using the test procedure are given in the table below and are expressed as minimum inhibitory concentrations (MIC) in micrograms/ml.

| Organism | | Test Compound MIC μg/ml | |
|---|---|---|---|
| | | 1 | 2 |
| S aureus | 663E | 0.1 | 0.1 |
| S faecalis | 850E | 1 | 16 |
| E coli | 1852E | 0.5 | 2 |
| E coli TEM1 | 1919E | 1 | 1 |
| E cloacae | 3647 | 1 | 4 |
| P aeruginosa | 1911E | 8 | 16 |
| C perfigens | 615E | 0.1 | 0.5 |
| B fragilis | 2017E | 0.2 | 0.5 |

Test compound 1 is the compound of Example 1
Test compound 2 is the compound of Example 2

The compounds of the invention are essentially non-toxic at therapeutically useful doses. For example no adverse effects were observed when the compound of Example 1 was administered to the mouse and rat at a dose of 500 mg/kg intravenously.

We claim:

1. A compound of formula (1):

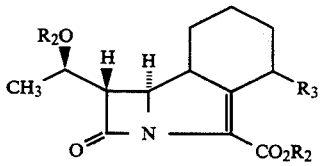

(I)

in which:
$R_1$ represents a hydrogen atom or a hydroxyl protecting group;
$R_2$ represents a hydrogen atom or a carboxyl protecting group; and
$R_3$ represents the group $-N(R_4)-CH=NR_5$, in which $R_4$ represents a hydrogen atom, and $R_5$ represents a $C_{1-4}$ alkyl group, or $R_4$ represents a $C_{1-4}$ alkyl group and $R_5$ represents a hydrogen atom;
or a salt, metabolically labile ester or solvate thereof.

2. A compound as claimed in claim 1 wherein $R_1$ and $R_2$ are hydrogen; or a physiologically acceptable salt, metabolically labile ester or solvate thereof.

3. A compound as claimed in claim 1 wherein $R_4$ is a methyl group and $R_5$ is hydrogen, or $R_4$ is hydrogen and $R_5$ is a methyl group.

4. A compound as claimed in claim 1 wherein $R_4$ is a methyl group and $R_5$ is hydrogen.

5. A compound as claimed in claim 1 wherein $R_1$ and $R_2$ are hydrogen; or a physiologically acceptable cation or an internal salt thereof.

6. A compound as claimed in claim 1 having a configuration (1b):

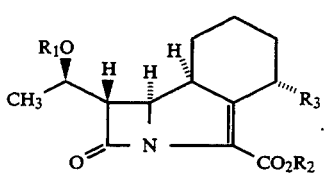

(1b)

7. (4S,8S,9R,10S,12R)-4-(N-methylformamidino)-10-(1-hydroxyethyl)-11-oxo-1-azatricyclo[7.2.0.0$^{3,8}$]undec-2-ene-2-carboxylic acid, or a physiologically acceptable salt, metabolically labile ester or solvate thereof.

8. A pharmaceutical composition comprising an effective amount of a compound as claimed in claim 2 in admixture with one or more physiologically acceptable carriers or excipients.

9. A pharmaceutical composition comprising an effective amount of a compound as claimed in claim 3 in admixture with one or more physiologically acceptable carriers or excipients.

10. A pharmaceutical composition comprising an effective daily amount of a compound as claimed in claim 4 in admixture with one or more physiologically acceptable carriers or excipients.

11. A pharmaceutical composition comprising an effective amount of a compound as claimed in claim 5 in admixture with one or more physiologically acceptable carriers or excipients.

12. A pharmaceutical composition comprising an effective amount of a compound as claimed in claim 6 in admixture with one or more physiologically acceptable carriers or excipients.

13. A pharmaceutical composition comprising an effective amount of a compound as claimed in claim 7 in admixture with one or more physiologically acceptable carriers or excipients.

14. A method of treatment of a human or non-human animal body to combat bacterial infections, which comprises administering to said animal body an effective amount of a compound as claimed in claim 2.

15. A method of treatment of a human or non-human animal body to combat bacterial infections, which comprises administering to said animal body an effective amount of a compound as claimed in claim 3.

16. A method of treatment of a human or non-human animal body to combat bacterial infections, which comprises administering to said animal body an effective amount of a compound as claimed in claim 4.

17. A method of treatment of a human or non-human animal body to combat bacterial infections, which comprises administering to said animal body an effective amount of a compound as claimed in claim 5.

18. A method of treatment of a human or non-human animal body to combat bacterial infections, which comprises administering to said animal body an effective amount of a compound as claimed in claim 6.

19. A method of treatment of a human or non-human animal body to combat bacterial infections, which comprises administering to said animal body an effective amount of a compound as claimed in claim 7.

20. A method as claimed in claim 14 which comprises treating a human and wherein the effective daily amount is 5 to 100 mg per kg of body weight.

* * * * *